United States Patent
Judd et al.

(10) Patent No.: US 10,603,858 B2
(45) Date of Patent: Mar. 31, 2020

(54) METHOD OF DETECTING TIRE MOLD BLADDER LEAKAGE BY SMELL

(71) Applicant: Compagnie Generale des Etablissements Michelin, Clermont-Ferrand (FR)

(72) Inventors: David Judd, Mauldin, SC (US); Roger Hartman, II, Tewksbury, MA (US)

(73) Assignee: Compagnie Generale Des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 16/334,137

(22) PCT Filed: Sep. 28, 2017

(86) PCT No.: PCT/US2017/053895
§ 371 (c)(1),
(2) Date: Mar. 18, 2019

(87) PCT Pub. No.: WO2018/064264
PCT Pub. Date: Apr. 5, 2018

(65) Prior Publication Data
US 2019/0366663 A1    Dec. 5, 2019

Related U.S. Application Data

(63) Continuation of application No. PCT/US2016/054587, filed on Sep. 30, 2016.

(51) Int. Cl.
*B29D 30/06* (2006.01)
*F16K 37/00* (2006.01)
(Continued)

(52) U.S. Cl.
CPC ..... *B29D 30/0662* (2013.01); *B29D 30/0654* (2013.01); *A61B 2562/12* (2013.01);
(Continued)

(58) Field of Classification Search
CPC ............ B29D 30/0654; B29D 30/0662; B29D 2030/0659; G01M 3/04; G01M 3/20
See application file for complete search history.

(56) References Cited

U.S. PATENT DOCUMENTS 4,221,124 A    9/1980    Jones
5,417,900 A *  5/1995    Martin, Sr. ........ B29D 30/0662
                                                  264/40.5
(Continued)

FOREIGN PATENT DOCUMENTS

WO    2016145300 A2    8/2001

OTHER PUBLICATIONS

European Patent Office; International Search Report and Written Opinion for patent application PCT/US2016/054587; dated Jun. 7, 2017; Publisher: European Patent Office, Rijswijk, Netherlands, pp. 1-11, enclosed.

(Continued)

*Primary Examiner* — James P Mackey
(74) *Attorney, Agent, or Firm* — Neal P. Pierotti

(57) ABSTRACT

A method of detecting tire mold (10) bladder (14) leakage is provided that includes placing an uncured tire (12) into a mold (10), and inflating a bladder (14), that has a fluid (22), within the mold. Sufficient heat and pressure are applied to at least partially cure the tire when the uncured tire is in the mold (10). The mold (10) is opened and electronic smelling is conducted on the at least partially cured tire (12). The electronic smelling is performed in order to determine whether the bladder (14) is leaking the fluid (22).

14 Claims, 6 Drawing Sheets

(51) Int. Cl.
    *F17D 5/02*   (2006.01)
    *G01M 3/04*   (2006.01)
(52) U.S. Cl.
    CPC .. *B29D 2030/0659* (2013.01); *F16K 37/0083* (2013.01); *F16K 37/0091* (2013.01); *F17D 5/02* (2013.01); *G01M 3/04* (2013.01)

(56) References Cited

U.S. PATENT DOCUMENTS

| | | |
|---|---|---|
| 6,330,821 B1 | 12/2001 | Arnold |
| 6,401,524 B1 | 6/2002 | Incavo |
| 7,987,697 B2 * | 8/2011 | Pickel ............... B29D 30/0662 73/40 |
| 2006/0037382 A1 | 2/2006 | Falchi |
| 2010/0005863 A1 | 1/2010 | Pickel |
| 2014/0041738 A1 | 2/2014 | Coleman |
| 2016/0223424 A1 | 8/2016 | Hilgers |

OTHER PUBLICATIONS

European Patent Office; International Search Report and Written Opinion for patent application PCT/US2017/053895; dated Jan. 1, 2015; Publisher: European Patent Office, Rijswijk, Netherlands, pp. 1-11, enclosed.

\* cited by examiner

METHOD OF DETECTING TIRE MOLD BLADDER LEAKAGE BY SMELL

CROSS-REFERENCE TO RELATED APPLICATIONS

The present application is a 35 U.S.C. § 371 application of PCT/US17/53895 filed on Sep. 17, 2017 and entitled "Method of Detecting Tire Mold Bladder Leakage by Smell." PCT/US17/53895 claims the benefit of PCT/US16/54587 filed on Sep. 30, 2016 and entitled "Method of Detecting Tire Mold Bladder Leakage by Smell." PCT/US17/35162 and PCT/US16/54587 are incorporated by reference herein in their entireties for all purposes.

FIELD OF THE INVENTION

The present invention relates generally to the detection of a leak in a bladder used to mold a tire. More particularly, the present application involves a method of using a smell detector to sense whether a bladder in a mold has leaked so that the bladder can be repaired in order to prevent the production of tires that may be under cured.

BACKGROUND

The production of tires includes the step of placing an uncured tire within a mold at which time heat and pressure is applied to the uncured tire in order to change its state to a cured condition. During the curing process, the uncured tire is placed inside of a metal mold that surrounds the exterior of the uncured tire. An expandable rubber bladder is positioned inside of the uncured tire, when it is within the mold, and can be expanded in order to apply pressure to the inside surface of the uncured tire. Steam, hot water, or inert gas can be transferred into the expandable bladder in order to cause it to assume an expanded state. The pressure applied by the expandable bladder forces the uncured tire against the mold to cause the uncured tire to be under pressure forces. Heat may be simultaneously applied, and the combination of heat and pressure applied for a particular time effects the curing process. The cured tire may then be removed from the mold and transported downstream for subsequent processing.

The expandable bladder may be punctured, or can otherwise leak, thus causing the expandable bladder to exert less pressure on the uncured tire than originally intended. Since less pressure is being applied to the tire during the curing process, the tire may not be fully cured and must be scrapped. In production, it may be the case that six or seven tires are under cured through use of a damaged expandable bladder before the leak is caught resulting in all of these tires being scrapped. Tire production facilities automatically scrap a tire that is molded through the use of a leaking bladder.

One method of detecting a leaking bladder may be through visual inspection of the tire. Although effective, such method is time consuming, and due to a cooling circuit buffer between curing and inspection six or seven under cured tires will be produced that must be scrapped. Another method of detecting a leaking bladder is by the measurement of humidity. The amount of humidity detected over the ambient level at each press extraction can be measured and if a threshold level is sensed then it can be assumed the bladder is leaking. This method thus senses the amount of steam or moisture released from a leaking bladder. Although capable of sensing a leaking bladder, this technique is not considered industrially robust and sometimes may classify a non-leaking bladder as a leaking bladder.

Another way of determining whether the expandable bladder is leaking is by counting the number of steam, hot water, or inert gas injections during curing of the tire. If the number of pressure increases that are needed to keep the expandable bladder pressurized moves beyond a threshold number it can be determined that the expandable bladder is leaking. Although capable of catching large leaks of the expandable bladder, this method may not be capable of detecting smaller leaks of the expandable bladder and thus is not dependable. Although mechanisms of detection of bladder leakage exist, none of them allow for the detection of a bladder leak that results in reliable detection of an expandable bladder leak with minimum tire scrap. As such, there remains room for variation and improvement within the art.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGS. in which.

Figure 1:
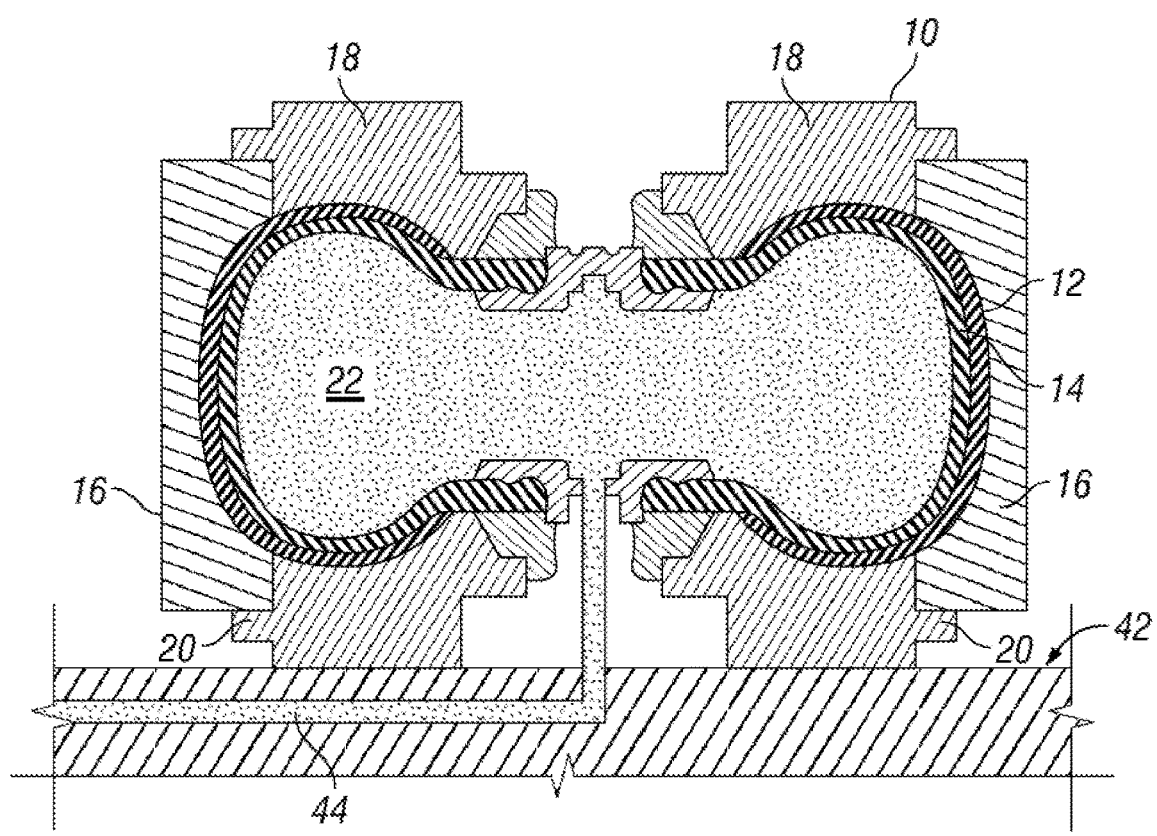
FIG. 1 is a side view in partial cross-section of a tire being molded with a mold that includes a bladder that is not leaking.

Repeat use of reference characters in the present specification and drawings is intended to represent the same or analogous features or elements of the invention.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

A method of monitoring to determine whether a bladder 14 of a tire mold 10 is leaking is provided. The method involves removing a tire 12 from a mold 10 and transporting the tire 12 away from the mold 10 so that the tire 12 does not contact or otherwise engage the mold 10. Electronic sensing of the tire 12 is conducted in order to determine whether the mold 10 from which the tire 12 is produced has or does not have a leaking bladder 14. The method accomplishes this task by sensing an odor indicative of a bladder 14 leak. In this regard, a bladder 14 that is leaking will produce an odor that may be carried by the tire 12 for some amount of time. This odor may be a distinct odor that fades with time. This odor can be electronically sensed when the tire 12 is away from the mold 10, and if it is in fact sensed, the method will determine that the bladder 14 from the mold 10 that produced the tire 12 is leaking. If the tire 12 is electronically sensed and the odor of a leaking bladder 14 is not detected, then the method may determine that the tire 12 was not produced from a mold 10 that features a leaking bladder 14, and thus consequentially that the bladder 14 is not leaking.

FIG. 1 shows a mold 10 for curing a tire 12. A tire 12 that is made of uncured rubber is placed into the mold 10 and cured via heat and pressure applied by the mold 10. The mold 10 can be configured in a variety of ways. In the embodiment illustrated, the mold 10 includes a series of tread segments 16 that engage tread portions of the tire 12 to form the tread of the tire 12. The mold 10 also includes a plurality of top segments 18 and a series of bottom segments 20 that engage the sidewalls of the tire 12. In some instances, the bottom segments 20 may not be a number of segments but could instead be a single continuous segment. The segments 16, 18 and 20 may move towards or away from one another in order to open up the mold 10 to allow the mold 10 to close onto the tire 12 and apply pressure to the tire 12. Heating elements can be located within the various segments 16, 18 and 20 or they may be otherwise heated in order to transfer heat into the tire 12 that is within in the mold 10. In this manner, the mold 10 is capable of applying heat and pressure to the tire 12 that is within the mold 10. Although described as all being moveable, it may be the case that some of the segments 16, 18 and/or 20 are not movable while others are in fact movable to open and close the mold 10. The segments 16, 18 and/or 20 may be movable in that they move relative to the ground 42 onto which the mold 10 rests.

The mold 10 additionally includes a bladder 14 that is located within the interior portion of the mold 10 so as to be generally located inside of a mold cavity formed by the tread segments 16, top segments 18, and bottom segments 20. The bladder 14 is a flexible membrane that has an interior in fluid communication with a supply source or pressure source via a conduit 44. The bladder 14 is in the expanded state in FIG. 1 in which it is pressurized and includes fluid 22. The bladder 14 is pressurized to the point that it presses against the inner walls of the tire 12 that is in the mold 10. The bladder 14 thus forms an interior surface against which the tire 12 is pressed via application of pressure to the exterior of the tire from the segments 16, 18 and 20. The bladder 14 may also apply its own pressure to the interior of the tire 12 to cause the tire 12 to be compressed between all of the elements 14, 16, 18 and 20.

The fluid 22 located within the bladder 14 can be any type of fluid such as air, water, steam, or nitrogen. Further, the fluid 22 may be any combination of fluids such as being both water and steam, or some combination of air and nitrogen. Fluid 22 can be injected into the bladder 14 through the conduit 44 in order to increase pressure within the bladder 14 and cause it to expand and act against the interior of the tire 12. The conduit 44 and bladder 22 may be located in the same position with respect to the ground 42, or may move as well relative to the ground 42 when the mold 10 is moved between the closed and open positions. Although shown as having but a single aperture that functions as both and inlet and exit for the fluid 22, the bladder 14 can have two or more openings in other embodiments into which fluid 22 may flow. These openings may be dedicated inlets and outlets, or may all of the various openings may function as both inlets and outlets.

Figure 2:
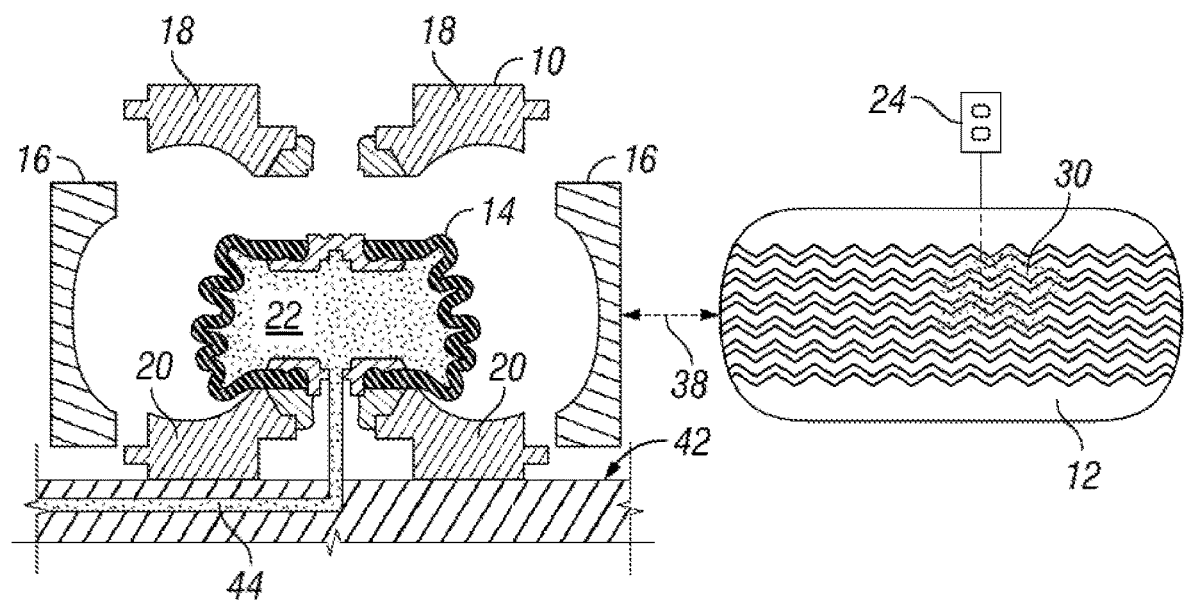
FIG. 2 is a side view in partial cross-section of the mold of FIG. 1 opened with the tire removed and electronic sensing being conducted on the tire.

The bladder 14 is not punctured in the mold 10 of FIG. 1 and none of the fluid 22 or other contents of the interior of the bladder 14 engages the tire 12 during the curing process. Once the tire 12 has been cured for a sufficient amount of time, the mold 10 can be opened. FIG. 2 shows the mold 10 of FIG. 1 opened and the tire 12 removed. The mold 10 can open in a variety of manners such as by having the top segments 18 moved upwards relative to the ground 42, and the tread segments 16 moved away from one another in relation to the ground 42. The bottom segments 20 do not move, but could move relative to the ground 42 in other arrangements. The pressure applied to the bladder 14 is removed by venting fluid 22 from the interior of the bladder 14 out of the conduit 44. The bladder 14 will contract in size and this may remove pressure on the tire 12. Opening of the segments 16, 18 and 20 will provide space sufficient for one to then remove the tire 12 from the mold 10 by either automatic or manual means. The curing of the tire 12 may be complete once the mold 10 is opened and the tire 12 is removed. However, in some instances, the tire 12 is not fully cured upon removal from the mold 10. Upon removal, the tire 12 will still be warm and will still be completing its curing process even after it has been removed from the mold 10 and moved downstream into a waiting cue or to a subsequent processing station. As such, the tire 12 may be described as at least partially cured upon exiting the mold 10 because it will either be fully cured or not fully cured upon exiting but at least a portion of the curing will be accomplished in the mold to give it this designation.

The tire 12 upon exiting the mold is moved a distance 38 away from the mold 10 and is not located within the mold 10 and does not engage the mold 10. In this regard, the tire 12 is free from engagement with the segments 16, 18 and 20 of the mold when positioned at distance 38. The tire 12 is also not in engagement with the bladder 14, and the bladder 14 is not located within the tire 12 when the tire 12 is removed from the mold 10 and is located at distance 38 from the mold 10. The tire 12 in FIGS. 1 and 2 is produced from a mold 10 that includes a bladder 14 that does not leak any of the fluid 22. The tire 12 has an odor present in the particulates 30 that emanate from the tire 12. Electronic sensing may be conducted on the particulates 30 to determine whether a particular odor is present. As the leaking of a bladder 14 causes a distinct odor, this odor may be carried by the tire 12 and recognized by electronically sensing the tire 12 when the tire 12 is at the distance 38 from the mold 10 as the tire 12 will carry this odor of a leaking bladder 14 for some amount of time. The distance 38 can be measured in a straight line, or may be measured as the distance the tire 12 travels from the mold 10. In this regard, the tire may move three feet vertically, then laterally three feet from the mold 10 and thus the distance 38 in this regard is six feet. The distance 38 may be from 0.5 meters to 100 meters in certain arrangements. Distance 40 can be measured in the same manners as mentioned with distance 38.

The electronic sensing of the tire 12 can be executed by any mechanism or combination of mechanisms. In some embodiments, the electronic sensing is by way of an electronic nose 24 that senses the odor present and processes this odor to determine whether it is the odor of a ruptured bladder 14 and outputs the results of this analysis. In other variations, an electronic sensor may sense the odor and then transmit this information to a separate processor that performs an analysis of the data and determines whether an odor is present that is indicative of a leaking bladder 14. Still further, in some variations a separate display and output mechanism can be present to output the decision made by the processor as to whether the odor in question is present to indicate the bladder 14 is leaking.

The electronic nose 24 is located a distance from the mold 10 so that the electronic nose 24 does not engage the mold 10 and is not located inside of the mold 10. The distance may be a greater distance than the distance 38, may be the same distance as distance 38, or may be less distance than distance 38 in accordance with various exemplary embodiments. In FIG. 2, the electronic nose 24 includes a probe that is located inside of the tire 12 approximately at its midpoint in the lateral direction. The probe may be against the interior of the crown of the tire 12 in some instances. In other arrangements, the probe and all parts of the electronic nose 24 are outside of the tire 12 and can be against and in contact with a portion of the tire 12, such as the sidewall, or may be completely out of engagement with the tire 12. As shown, the particulates 30 that emanate from the tire 12 do not include an odor that from a leaking bladder 14, and the electronic nose 24 upon analyzing the particulates 30 indicate that the tire 12 was partially cured by a mold 10 that does not include a leaking bladder 14. The production of tires 12 may be arranged so that multiple molds 10 are used to cure tires 12 at the same time. Once cured, the tires 12 are removed from the molds 10 and transported to a common area in a line. This location of common area through which all of the tires 12 of a curing bank of tires 12 from multiple molds 10 is transferred or passes through may be described as being the head of the line. If the electronic nose 24 is located at the head of the line, then a single electronic nose 24 may conduct smelling of the tires 12 at this location allowing for only a single electronic nose 24 to be employed. Alternatively, an electronic nose 24 could be located proximate to, although not touching, each one of the molds 10 so that each mold 10 is associated with its own electronic nose 24. Such a design would allow fewer bad tires 12 to be scrapped as the tires 12 would be sniffed almost immediately upon exiting their molds 10, but such a design may be more costly as multiple electronic noses 24 are needed instead of a single electronic nose 24. It may also be envisioned that some combination can be employed where more than one electronic nose 24 is used to sniff tires 12 before the head of the line, but in which all of the molds 10 do not have their own dedicated electronic nose 24.

Figure 3:
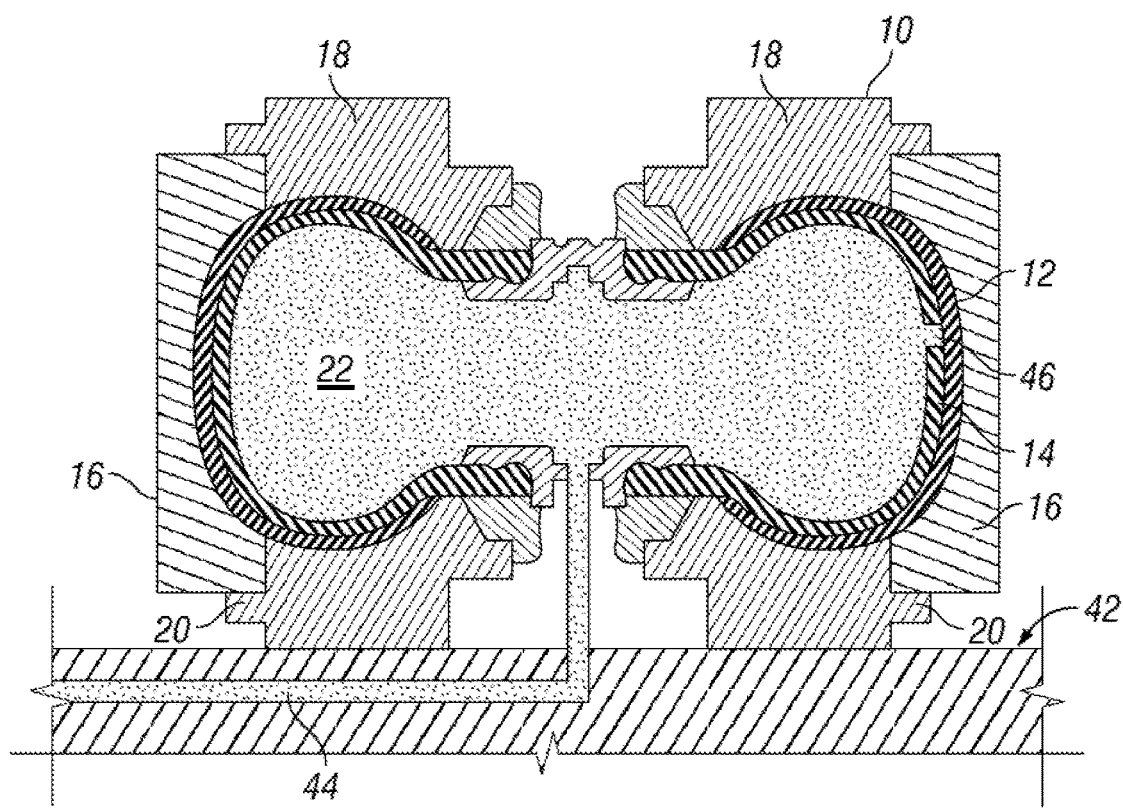
FIG. 3 is a side view in partial cross-section of a tire being molded with a mold that includes a bladder that is leaking.
Figure 4:
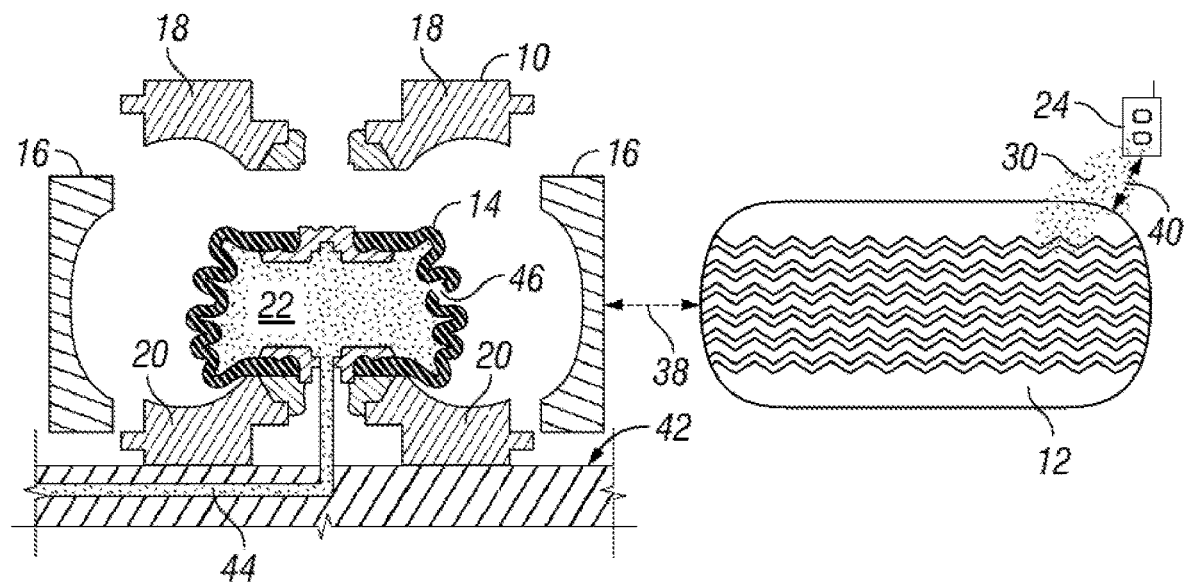
FIG. 4 is a side view in partial cross-section of the mold of FIG. 3 opened with the tire removed and electronic sensing being conducted on the tire.

Objects may engage the bladder 14 and cause a puncture 46 to be made through the bladder 14. Further, the bladder 14 may fail in wear simply by being expanded and contracted a number of times to cause a puncture 46 through the wall of the bladder. FIG. 3 shows a mold 10 with a bladder 14 that has a puncture 46. Although only a single puncture 46 is shown, multiple punctures 46 may be located through the bladder 14 in some instances. The puncture 46 can be of any size, and the fluid 22 is capable of escaping the bladder 14 at different flow rates. Also, although described as being a puncture 46 through the bladder 14, the leaking bladder 14 may leak fluid 22 from areas between the engagement of the membrane of the bladder 14 and the mold 10, or other portions of the mold 10 may leak fluid 22 that are not part of the membrane of the bladder 14. In these instances, it is still understood that the resulting fluid 22 leaking is described as a leaking bladder 14 even though the membrane of the bladder 14 is not actually punctured.

When the bladder 14 is inflated and the tire 12 is being cured by the mold 10, the fluid 22 may engage the tire 12 and cause the tire 12 to have particulates 30 that include molecules of the fluid 22. The particulates 30 that include the odor of the fluid 22 can be in any amount on the tire 12 and may be located on its inner surface, or can pass through the tire to its outer surface or be otherwise disposed onto the outer surface as the fluid 22 may leak and spray onto the outer surface of the tire 12 when the mold 10 is opened and the tire 12 begins to move out of the mold 10.

Once cured to a desired degree, the mold 10 is opened as previously discussed, and the tire 12 is removed from the mold 10 and transported a distance 38 from the opened mold 10 so that the tire 12 does not engage the mold 10. An electronic nose 24 can be placed a distance 40 from the tire 12 so that it does not engage the mold 10, and the electronic nose 24 may again be used to smell the airborne particulates 30. The distances 38 and 40 may be the same as those previously described with respect to FIGS. 1 and 2 in which the mold 10 was not leaking. The electronic nose 24 upon sensing the airborne particulates 30 this time may determine that the airborne particulates 30 include an odor indicative of a leak of the bladder 14 and may alert the operator that the bladder 14 is in fact leaking. Upon detection of a leaking bladder 14, the tire 12 that is being currently smelled by the electronic nose 24 can be scrapped as it was made through use by a defective bladder 14. Additionally, if a tire 12 is currently being molded in the mold 10, it too may be scrapped as it is being cured through the use of a defective bladder 14. With such a system, only 1 or 2 tires 12 need to be scrapped. In certain embodiments depending upon where the electronic nose 24 is situated with respect to the mold 10, from 3-5, from 6-7, or up to 8 tires will need to be scrapped through use of the provided method.

Figure 10:
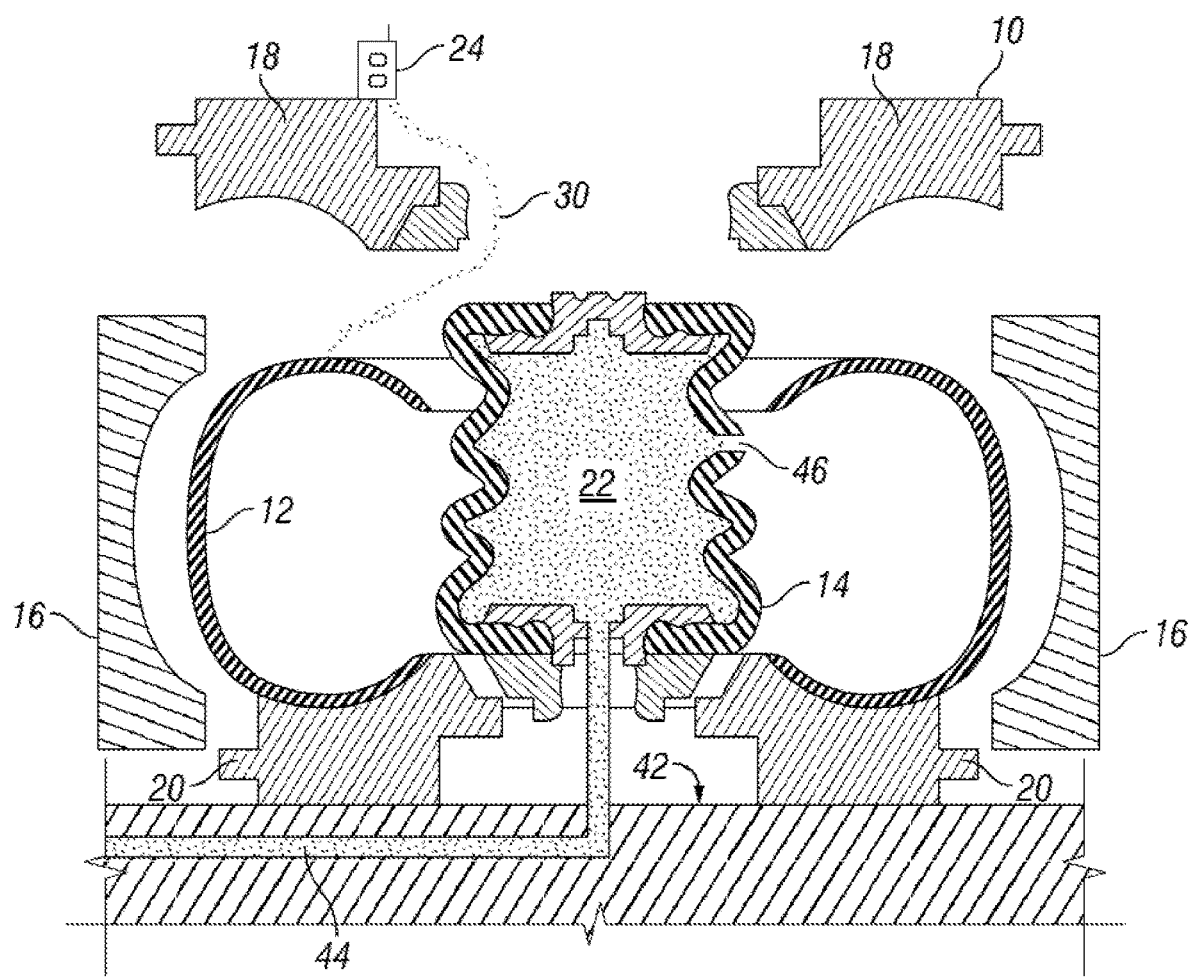
FIG. 10 is a side view in partial cross-section of a tire in a mold after opening of the mold that is being smelled by an electronic nose.

Although described as being a distance 38 from the mold 10, the tire 12 need not be a distance 38 from the mold 10 when sensed, but instead may be at the mold 10 when sensed. FIG. 10 shows a variation of the method in which the tire 12 is located at the mold 10 when sensed. In this embodiment, the tire 12 is cured by the mold 10 through the application of heat and pressure from the tread segments 16 and the inflated bladder 14. Once the curing process is completed through the application of the heat and pressure, the mold 10 is opened so that the tread segments 16 move away from the tire 12, and so that the bladder 14 deflates. The tire 12 may still be sitting in the mold 10 at this point so that the tire 12 is in engagement with the mold 10. The airborne particulates 30 may be sensed by the sensor 24, and the sensor 24 could be in engagement with the portions of the mold 10, such as the top segments 18, when the airborne particulates 30 are sensed. After sensing the particulates 30, which may be odor of the uncured portions of the rubber of the tire 12 from the heat and pressure, or which may be odor from the inside of the bladder 14, the tire 12 can be removed from the open mold 10 and disposed of or used depending upon the data from the sensor 24.

In the various embodiments, the airborne particulates 30 that are measured may be from uncured rubber of the tire 12 that was not cured via the heat and pressure applied in the mold 10. In other embodiments, the airborne particulates 30 may be from the fluid 22 that leaks from the bladder 14. In other embodiments, the airborne particulates 30 that are sensed to determine whether the bladder 14 is leaking may be a combination of both smelling uncured rubber and from the fluid 22 from the bladder 14.

Figure 5:
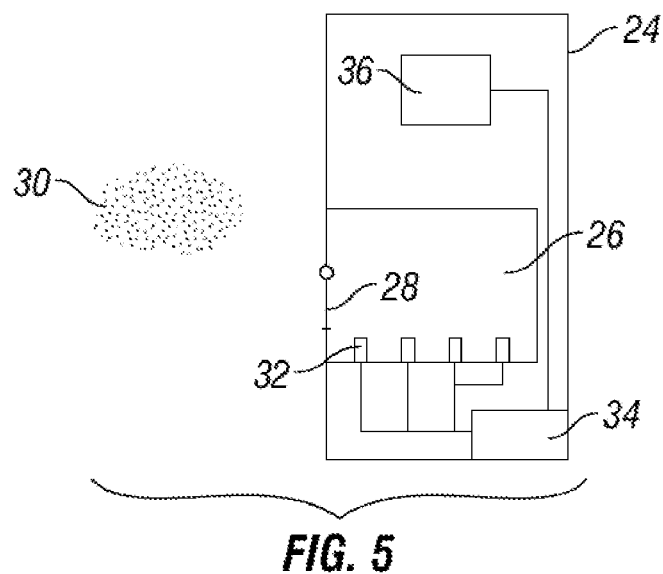
FIG. 5 is a front view of an electronic nose before electronic smelling of an odor is conducted.

The electronic nose 24 is shown in greater detail with reference to FIG. 5. The electronic nose 24 has a sample chamber 26 that initially is empty of any of the airborne particulates 30 which are instead located outside of the electronic nose 24. A series of sensors 32 can be located within the sample chamber 26 and may be in communication with a processor 34. The electronic nose 24 may optionally include a display 36 in communication with the processor 34 to indicate to a user whether a particular odor is present, to convey what is causing the particular odor, and to afford a mechanism of communication to the user to configure or operate the electronic nose 24. In some embodiments, the electronic sensor 24 may be a CYRANOSE® 320 electronic nose developed by Cyrano Sciences located in Pasadena, Calif., USA and distributed by Sensigent Intelligent Sensing Solutions having offices located at 1438 Arrow Highway, Baldwin Park, Calif., 91706, USA.

Figure 6:
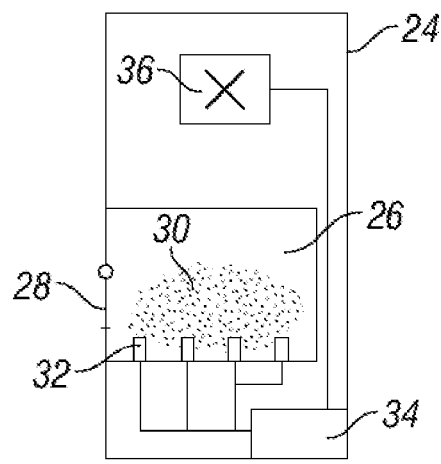
FIG. 6 is a front view of the electronic nose of FIG. 5 in which the particulates are placed into a sample chamber and analyzed.

The electronic nose 24 has a door 28 that is closed as shown in FIG. 5 and prevents airborne particulates 30 from entering the sample chamber 26. When the tire 12 is moved into the desired location, the door 28 can be opened to allow airborne particulates 30 to flow through the open door 28 and into the sample chamber 26. The airborne particulates 30 are shown inside of the sample chamber 26 in FIG. 6. In other embodiments, vacuum or some other type of pumping mechanism may be employed to aid transfer of the airborne particulates 30 into the sample chamber 26. In still other embodiments, a sample chamber 26 need not be employed and the airborne particulates 30 may simply be disposed against the sensors 32. In some embodiments, thirty two sensors 32 can be present and may be used to absorb the airborne particulates 30 for sensing purposes. In other arrangements, any number of sensors 32 can be used, for example up to thirty two sensors can be used, sixteen sensors can be used, or any other number in other embodiments. When the sensors 32 absorb the airborne particulates 30, their resistance changes and this information is communicated to the processor 34 to allow the processor 34 to determine which type of airborne particulate 32 has been absorbed. Each sensor 32 reacts differently to each type of airborne particulate 32 giving a 32 dimensional smell space. Once the processor 34 has determined the type of airborne particulate 32 in the sample chamber 26, this information may be communicated to the display 36 or other output device apart from the electronic nose 24. If the airborne particulate 32 is indicative of a leaking bladder 14, then this information can be communicated to an operator to instruct the operator to stop the line and repair the damaged mold 10, or the information may be used to automatically shut down the line and instruct the operator that a leak has been detected.

The electronic nose 24 may classify smells with any one of three clustering techniques—K nearest neighbors (KNN), K-means, or canonical discriminant analysis (CDA). The KNN technique is a clustering algorithm that searches for a pint's nearest neighbors and whichever group the majority of the point's neighbors belong to is the group the point is classified into. The K-means technique is a clustering algorithm in which k random points are chosen as the mean centers of k groups. The CDA technique is a dimension reduction technique that maximizes the between class variance and minimizes the within class variance. The CDA technique works by finding two scatter matrices, the within class scattering matrix and the between class scattering matrix. Before the electronic nose 24 can recognize a smell it must first be exposed to the smell and told to remember that particular smell. Doing this allows the electronic nose 24 to build a training set of smells with which to compare to future sampling events. The electronic nose 24 can be exposed to airborne particulates 30 from tires 12 made from molds 10 that have bladders 14 that are not leaking, and can be exposed to airborne particulates 30 from tires 12 cured by molds 10 with leaking bladders 14 so that it becomes calibrated to smells that are indicative of a leaking bladder 14 and a non-leaking bladder 14.

Figure 7:
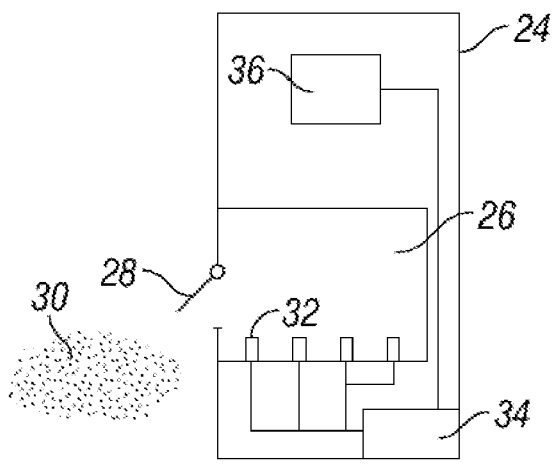
FIG. 7 is a front view of the electronic nose of FIG. 5 in which the particulates are purged from the sample chamber after being analyzed.

Once the tire 12 has been electronically sniffed and the presence of a particular smell detected or not detected, the sensors 32 may release the absorbed particles back into the air during a purge cycle. FIG. 7 shows the door 28 being opened and the airborne particulates 30 released from the sample chamber 26 during a purge cycle of the electronic nose 24. The release can be obtained by opening the door 28 and pushing the airborne particulates 30 out of the sample chamber 26 by a fan or by pressurizing the sample chamber 26 to cause the airborne particulates 30 to exit. The sensors 32 are now free from the airborne particulates 30 of the tire 12, and the door 28 closes to once again place the electronic nose 24 back into the FIG. 5 state of waiting for a new tire 12 to be sensed and thus waiting for a new set of airborne particulates 30 to be detected. The electronic nose 24 can be arranged so that it triggers a warning or shut off only when the airborne particulates 30 sensed are those affiliated with a leaking bladder 14 so that no other smells are output to the operator. In this manner, the method may be constructed so that it outputs only a result indicative of a leaking bladder 14 and no other outputs are sent. Before the electronic nose 24 begins conducting measurements, a separate baseline purge may take place in which air is run through a filter and over the sensors 32 to allow them to release old chemicals so that they will be ready for new ones. This baseline purge is not the same as the purge described with reference to FIG. 7, and it may be conducted when the line is down or tire 12 production otherwise stopped.

In other embodiments, a pair of lines can enter the sample chamber 26 that may not have the door 28. One line may have the air sample that is to be measured, and the other line may have purge air that is used to purge the sample chamber 26. A valve can be used to selectively distribute which one of these two lines goes into the sample chamber 26. Also, a line may be used to exit the contents of the sample chamber 26 to a location remote from the sample chamber 26 in these other arrangements.

Experiment Conducted in Accordance with One Exemplary Embodiment

An experiment was conducted in order to determine whether the asserted method was capable of detecting bladder 14 leakage in the production of tires 12. An electronic nose 24 that is a CYRANOSE® 320 was used to detect tires 12 made from leaking bladders 14 versus those made from non-leaking bladders 14. The experiment resulted in the detection of a bladder 14 leaking tire 12 75% of the time, and misclassified a healthy tire 12 as a bladder 14 leaking tire 12

16.7% of the time. The experiment made use of 5 tires in which 3 of the tires 12 were produced with a leaking bladder 14, and in which the other 2 tires 12 were made with a bladder 14 that was not leaking. In order to create the leaking bladder 14, the bladder 14 was cut with a pocket knife to create the puncture 46 in the bladder 14. The electronic nose 24 was located either right at the curing mold 10 or at the head of line.

In the experiment, two of the tires 12 were used to train the electronic nose 24—one from a mold 10 without defect, and the other from a mold 10 with a leaking bladder 14. The electronic nose 24 made 7 training smells of the tire 12 from the good mold 10. Two of these measurements were removed because they deviated too far from the mean. The process was repeated with the tire 12 made from the leaking bladder 14 in which ten measurements were taken with the two farthest form the mean removed.

To determine whether the training set was good, the data was run through a cross validation program executed by PCnose software which groups the training data points using one of the aforementioned clustering algorithms. It was found that of the 5 training data points for the tire 12 with no defect one was misplaced as having come from a leaking bladder 14, and of the 8 data points in the leaking bladder 14 tire 12 one was placed in the non-leaking bladder 14 category.

Once the electronic nose 24 was trained, four tires were used to test the ability of the electronic nose 24 to detect leaking bladder 14 tires. Two of the tires 12 were from non-leaking bladders (one was the same that was used in the training), and two of the tires 12 were from molds 10 with bladders 14 that leaked. The one good tire 12 that was also used for training was smelled one time, and the other tire 12 from the non-leaking bladder 14 was removed from the head of line and smelled three times. Of the two tires 12 made from the leaking bladder 14, one was removed immediately from the mold 10 and cooled for 90 seconds before it was smelled three times, and the other was removed from the head of line and smelled once.

The electronic nose 24 employed CDA in its analysis both for training and for testing. Settings on the electronic nose 24 were a substrate heater setting of 42 degrees Celsius, a baseline purge set to 10 seconds and a pump speed of high, the only sample draw was number 2 and it lasted 6 seconds at medium pump speed. The substrate heater is a regulator for the sensor 32 temperature so that the sensors 32 are set at the appropriate temperature for effective sensing. The first air intake purge lasted 10 seconds, and the second air sample purge lasted 30 seconds. Both the first and second intake and sample purges had pump speeds of high. The preprocessing was set to auto scale, normalization 1 was used, and the identification quality was medium.

Figure 8:
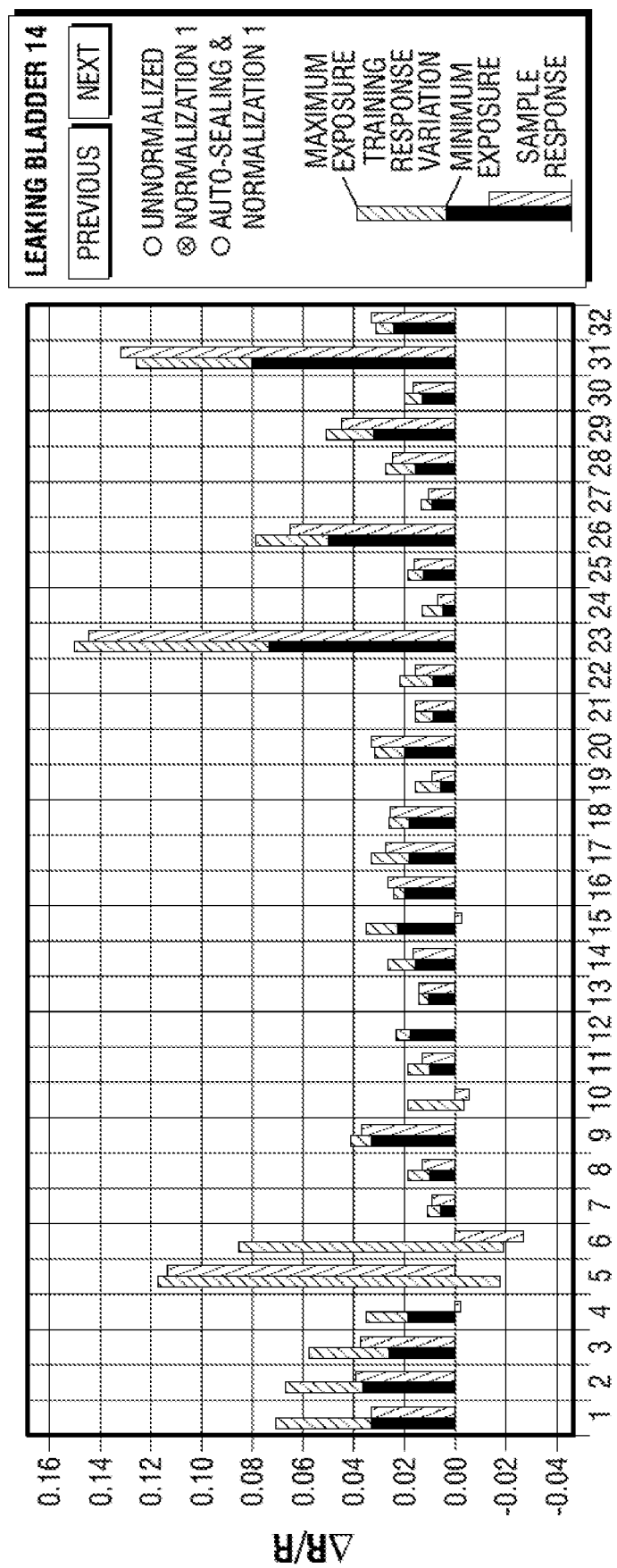
FIG. 8 is a graph of a smell print of a tire produced with a leaking bladder in the mold.

The first tire 12 tested was the same as the tire 12 in training that was made with a non-leaking bladder 14. This first tire 12 was classified as a good tire 2 out of 3 times. The third time it was tested it was classified as having been made from a bladder 14 that leaks, but the tire 12 had cooled significantly and had lost a considerable amount of its smell. The first tire 12 made from a leaking bladder 14 was identified correctly 2 out of 3 times as well, having been off the mold 10 about 120 seconds prior to running the test. The incorrect identification on this tire 12 was that of "unknown." FIG. 8 is a smell print of one of the successful tests of a tire 12 made with a leaking bladder 14. In FIG. 8, the red/cross hatched bars represent the smell of the tire 12. The black bars represent the minimum smell value during the training run for a tire 12 made from a leaking bladder 14. The gray/boxed in bars represent the maximum smell value during the training run.

Figure 9:
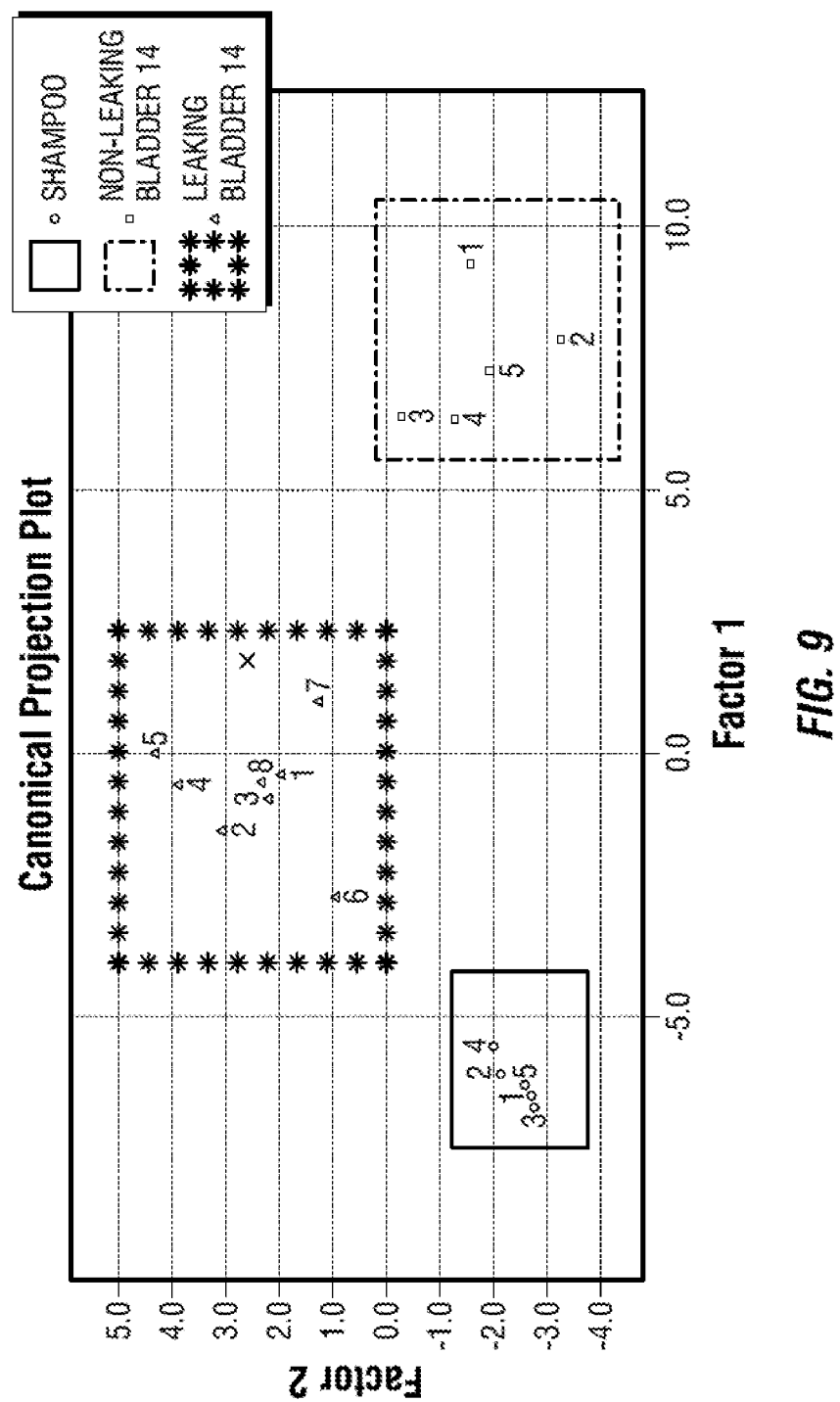
FIG. 9 is a CDA plot of a smell test of the tire tested in FIG. 8 in which its reading is shown at the "X" point.

FIG. 9 is a CDA plot of the smell test on a tire 12 made with a leaking bladder 14. The data points are shown for a tire 12 made with a bladder 14 that does not leak, training points for shampoo, and training points for a tire 12 made with a leaking bladder 14. The X is the test run data point showing that the tire 12 was in fact made from a mold 10 that has a leaking bladder 14. The CDA plot in FIG. 9 is the CDA plot of the run of FIG. 8.

After this tire 12 was run, another tire 12 made from a leaking bladder 14 was removed at the head of line and smelled once by the electronic nose and was correctly classified on the first smell. The next test was again done on a tire 12 pulled from the head of line, and this tire 12 was made from a mold 10 that did not have a leaking bladder 14. This tire 12 was classified as shampoo twice and as an unknown substance one time. The experiment carried out was able to correctly classify a tire 12 made from a leaking bladder 14 a majority of the time.

It is envisioned that other implementations of the disclosed method are possible in which a greater number of tires 12 are used to train the electronic nose 24. In some other embodiments, 10 tires 12 from non-leaking bladders 14 would be smelled once for training by the electronic nose 24 once they were fresh out of the mold 10, and 10 additional tires also from non-leaking bladders 14 would be smelled at the head of line. This process would be repeated for 10 tires 12 made from leaking bladders 14 that were smelled first thing after leaving the mold 10, and for 10 tires 12 made from leaking bladder 14 that are smelled at the head of line. This type of training would allow the electronic nose 24 to be trained at different areas in the plant so that it could recognize tires 12 from these different areas. From 4-10, from 11-20, or up to 100 tires 12 made from a leaking bladder 14 could be sampled by the electronic nose 24 in the detection method in order to determine whether the electronic nose 24 has been properly trained.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A method of detecting tire mold bladder leakage, comprising:
    placing an uncured tire into a mold;
    inflating a bladder within the mold, wherein the bladder has a fluid within the bladder;
    applying sufficient heat and pressure to the uncured tire to at least partially cure the tire when the uncured tire is in the mold;
    opening the mold; and
    electronically smelling by an electronic nose the at least partially cured tire after the step of opening the mold, wherein the step of electronically smelling by the electronic nose is performed in order to determine whether the bladder is leaking the fluid;
    wherein the electronically smelling comprising:
    drawing airborne particulates into a sample chamber;
    sensing the airborne particulates by a plurality of sensors;

processing data obtained from the plurality of sensors to determine if any of the airborne particulates are airborne particulates of the fluid or uncured rubber; and indicating that airborne particulates of the fluid or uncured rubber are present.

2. The method as set forth in claim 1, further comprising the step of removing the at least partially cured tire from the mold such that the at least partially cured tire is not located within the mold and does not engage the mold; wherein the step of electronically smelling takes place after the step of removing the at least partially cured tire from the mold such that the at least partially cured tire is not located within the mold and does not engage the mold.

3. The method as set forth in claim 2, wherein the electronically smelling begins 90 seconds or less from the point in time after the at least partially cured tire is removed from the mold such that the at least partially cured tire is not located within the mold and does not engage the mold.

4. The method as set forth in claim 2, wherein the electronically smelling begins at the point in time when the at least partially cured tire is located at a head of line, wherein the head of line is a location where tires coming out of multiple different molds assemble at a common location.

5. The method as set forth in claim 1, wherein the electronic nose is trained by having the electronic nose reference at least two reference tires at least partially cured by a reference mold that does not have a leaking bladder, and wherein the electronic nose is trained by having the electronic nose reference at least two different reference tires at least partially cured by a second reference mold that has a leaking bladder.

6. The method as set forth in claim 1, wherein the electronic nose is trained by having the electronic nose reference at least two reference tires at least partially cured by the mold.

7. The method as set forth in claim 1, wherein the bladder leaks the fluid and an odor of the fluid is carried by the at least partially cured tire, wherein the odor of the fluid is sensed by the electronically smelling to determine that the bladder is leaking the fluid.

8. The method as set forth in claim 1, wherein the electronically smelling comprising purging the airborne particulates from the sample chamber after the step of processing data.

9. The method as set forth in claim 1, wherein the step of electronically smelling determines that the bladder is not leaking the fluid.

10. The method as set forth in claim 1, wherein the tire is located in the opened mold when the step of electronically smelling is performed.

11. The method as set forth in claim 1, wherein the fluid is air.

12. The method as set forth in claim 1, further comprising stopping the production of tires with the mold such that two or fewer scrap tires are produced upon determining that the bladder is leaking the fluid by the electronically smelling.

13. The method as set forth in claim 1, wherein all parts of the electronic nose are outside of an interior space of the tire when the electronic nose electronically smells the tire.

14. A method of detecting tire mold bladder leakage, comprising:

placing an uncured tire into a mold;

inflating a bladder within the mold, wherein the bladder has a fluid within the bladder;

applying sufficient heat and pressure to the uncured tire to at least partially cure the tire when the uncured tire is in the mold;

opening the mold; and electronically smelling by an electronic nose the at least partially cured tire after the step of opening the mold, wherein the step of electronically smelling by the electronic nose is performed in order to determine whether the bladder is leaking the fluid;

wherein an odor of uncured rubber of the tire is sensed by the electronically smelling to determine that the bladder is leaking the fluid.

* * * * *